(12) United States Patent
Liang et al.

(10) Patent No.: US 10,472,321 B1
(45) Date of Patent: *Nov. 12, 2019

(54) HYDROXYTYROSOL P-PHENYLENEDICARBOXYLATE HAVING ANTIOXIDANT ACTIVITY AND A METHOD OF PREPARING THE SAME

(71) Applicants: Chengyuan Liang, Xi'an (CN); Yuzhi Liu, Xi'an (CN); Xingke Ju, Xi'an (CN); Yonghong Tang, Xi'an (CN); Minghui Chang, Xi'an (CN); Bin Tian, Xi'an (CN); Dan Yang, Xi'an (CN); Han Li, Xi'an (CN); Ning Liu, Xi'an (CN); Huayin Pu, Xi'an (CN); Jian Cha, Xi'an (CN); Juanna Song, Xi'an (CN); Yongbo Wang, Xi'an (CN)

(72) Inventors: Chengyuan Liang, Xi'an (CN); Yuzhi Liu, Xi'an (CN); Xingke Ju, Xi'an (CN); Yonghong Tang, Xi'an (CN); Minghui Chang, Xi'an (CN); Bin Tian, Xi'an (CN); Dan Yang, Xi'an (CN); Han Li, Xi'an (CN); Ning Liu, Xi'an (CN); Huayin Pu, Xi'an (CN); Jian Cha, Xi'an (CN); Juanna Song, Xi'an (CN); Yongbo Wang, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/510,907

(22) Filed: Jul. 13, 2019

(51) Int. Cl.
*C07C 271/26* (2006.01)
*B01J 31/02* (2006.01)
*C07C 269/02* (2006.01)

(52) U.S. Cl.
CPC ......... *C07C 271/26* (2013.01); *B01J 31/0237* (2013.01); *B01J 31/0244* (2013.01); *C07C 269/02* (2013.01)

(58) Field of Classification Search
CPC .................. C07C 233/019; C07C 231/06
See application file for complete search history.

(56) References Cited

PUBLICATIONS

Unruh et al., Thermally activated, single component epoxy systems, (Macromolecules (Washington, DC, United States) (2011)44(16), 6318-6325).*

* cited by examiner

*Primary Examiner* — Jafar F Parsa

(57) ABSTRACT

A compound having the formula (I):

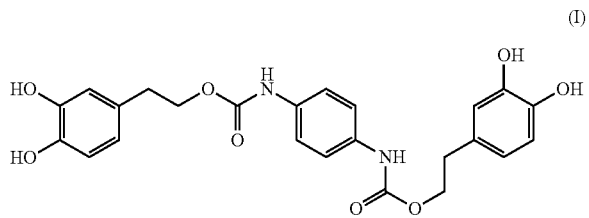

is disclosed. A method of preparing the compound of formula (I) is also disclosed.

10 Claims, 1 Drawing Sheet

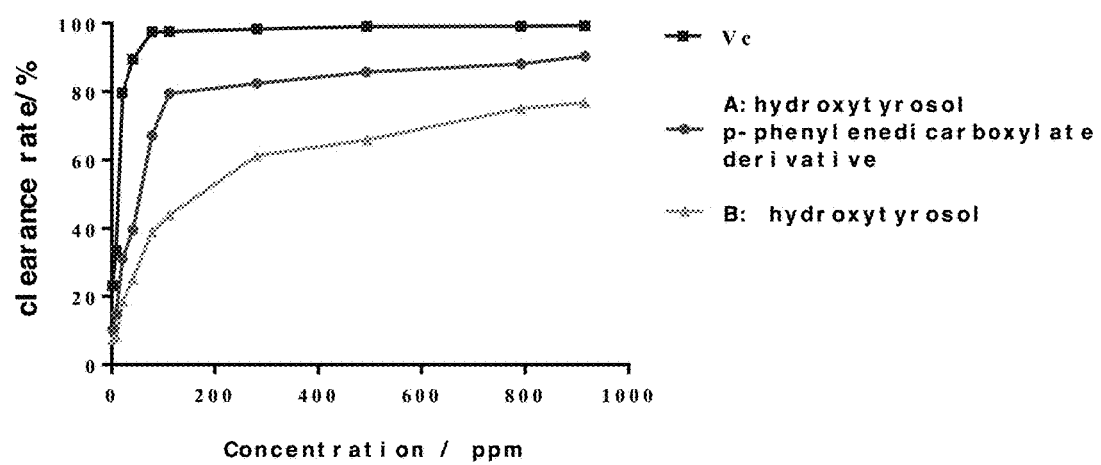

HYDROXYTYROSOL P-PHENYLENEDICARBOXYLATE HAVING ANTIOXIDANT ACTIVITY AND A METHOD OF PREPARING THE SAME

FIELD OF THE INVENTION

The present invention relates to food chemistry area, more specifically, hydroxytyrosol p-phenylenedicarboxylate having antioxidant activity and a method of preparing the same.

BACKGROUND OF THE INVENTION

Oil or fat, as one of the three main nutrients, is an essential part of the daily diet. Oxidation of oil and fat is an important factor affecting the quality of oils. The automatic oxidation of oil and fat is a spontaneous oxidation reaction of activated olefin-containing substrates (such as unsaturated oils) and oxygen in the air at room temperature without any direct illumination or any catalyst. The products produced by oxidation have an adverse effect on the flavor, color and texture of the edible oil and fat, resulting in shortening the shelf life and reducing the nutritional quality of the oil and fat. Oxidation of oil and fat can cause damage to membranes, enzymes and proteins, leading to many diseases of aging and even carcinogenicity, which harms human health. Therefore, prevention of oxidation of oil and fat in foods and fats is a major concern for human health, and the most common way to prevent oxidation of oils is to add antioxidants.

Hydroxytyrosol (4-(2-hydroxyethyl)-1,2-benzenediol; compound of formula (II)) is a phenylethanoid, a type of phenolic phytochemical with antioxidant properties in vitro. In nature, hydroxytyrosol is found in olive leaf and olive oil, in the form of its elenolic acid ester oleuropein and, especially after degradation, in its plain form.

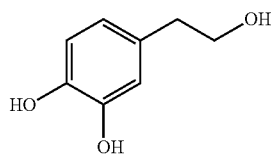

(II)

P-Phenylene diisocyanate (1,4-phenylene diisocyanate, PPDI) is a symmetrical aromatic diisocyanate. It reacts with a chain extender to synthesize a polyurethane elastomer with high cohesive energy and good heat resistance. The polyurethane PUE elastomer has good hardness, temperature resistance and dynamic performance, wear resistance, toughness, solvent resistance and heat and humidity resistance, and is a promising high-performance material.

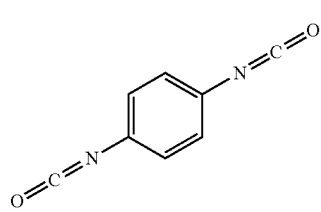

(III)

In the present invention, p-phenylene diisocyanate is modified by the hydroxytyrosol structure to obtain hydroxytyrosol p-phenylenedicarboxylate while eliminating the toxic group of p-phenylene diisocyanate. Hydroxytyrosol p-phenylenedicarboxylate has excellent antioxidant activity and high medical research and application value in the field of antioxidant products.

SUMMARY OF THE INVENTION

In one embodiment, present invention provides a compound having the following formula (I):

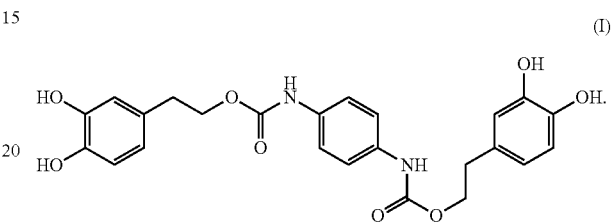

In another embodiment, the present invention provides a method of preparing the compound of formula (I). The method includes reacting the compound of formula (II) with the compound of formula (III) to obtain the compound of formula (I):

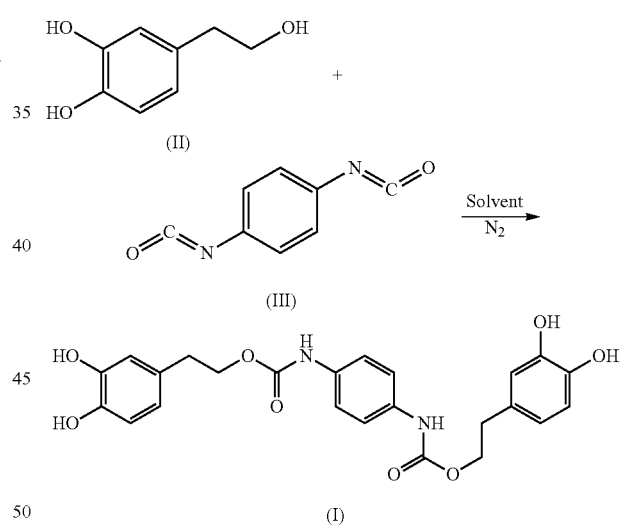

In another embodiment, the reaction of the compound of formula (II) with the compound of formula (III) includes the following steps: placing the compound of formula (II) and the compound of formula (III), in a molar ratio of 2.2:1 to 2.5:1, in a reactor to form a reaction mixture; adding an organic solvent and a catalyst to the reaction mixture under nitrogen atmosphere; heating the reaction mixture at 25-60° C. for 1-3 hours under sonication; concentrating the reaction mixture under reduced pressure to give a crude product; and purifying the crude product using silica gel fresh chromatography, eluting with a mixture of ethyl acetate and petroleum ether solvent to obtain the compound formula (I).

In another embodiment, the organic solvent is toluene, acetonitrile or tetrahydrofuran.

In another embodiment, the organic solvent is toluene.

In another embodiment, the molar ratio of the compound of formula (II) and the compound of formula (III) is 2.2:1.

In another embodiment, the catalyst is triethylamine or 4-dimethylaminopyridine.

In another embodiment, the catalyst is triethylamine.

In another embodiment, the reaction mixture is heated at 60° C.

In another embodiment, the reaction mixture is heated for 2 hours.

In another embodiment, the eluent is ethyl acetate:petroleum ether=1:6

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIG. 1 shows the DPPH Radical Scavenging Activities of Vitamin C (Vc), hydroxytyrosol p-phenylenedicarboxylate (A), and hydroxytyrosol (B).

DETAILED DESCRIPTION OF THE ILLUSTRATED EMBODIMENTS

Reference will now be made in detail to embodiments of the present invention, example of which is illustrated in the accompanying drawings. The following examples illustrate the present invention, but the present invention is not limited to the following examples.

Example 1

Preparation of Compound Hydroxytyrosol p-phenylenedicarboxylate (bis(3,4-dihydroxyphenethyl) 1,4-phenylenedicarbamate, Compound of Formula (I))

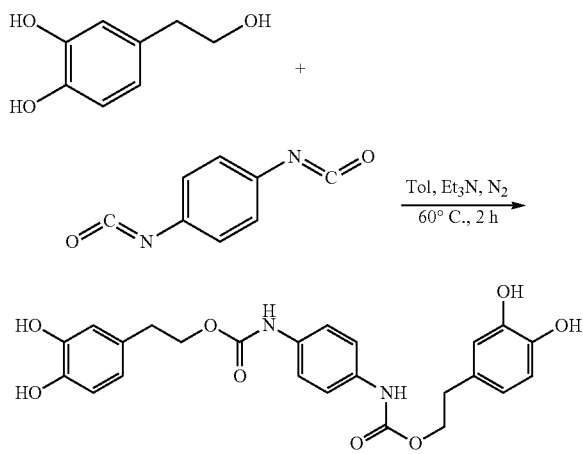

105.9 mg (0.68 mmol) hydroxytyrosol and 42 µL (0.30 mmol) triethylamine were dissolved in 50 mL of toluene in a 100 mL reactor to form a reaction mixture under nitrogen atmosphere. 50 mg (0.31 mmol) 1,4-phenylene diisocyanate in 5 mL toluene was slowly added dropwise to the reaction liquid by a separatory funnel. The reaction mixture was then heated at 60° C. for 2 hours. Thin layer chromatography was used to track the reaction to completion. The reaction mixture was concentrated under reduced pressure to give a crude product. The crude product was purified by silica gel fresh chromatography, eluting with petroleum ether:ethyl acetate=6:1 as eluent, and the eluent was concentrated under reduced pressure and dried to obtain 106.3 mg hydroxytyrosol p-phenylenedicarboxylate, a yield of 73.21%.

$^1$H-NMR (400 MHz, DMSO-$d_6$) δ (ppm): 9.31 (2H, br), 7.71 (4H, s), 6.94 (2H, s), 6.86 (2H, d), 6.77 (2H, d), 5.32 (4H, s), 4.50 (4H, t), 2.91 (4H, t); $^{13}$C-NMR (400 MHz, DMSO-$d_6$) δ (ppm): 154.9, 146.4, 144.7, 134.8, 132.2, 122.4, 121.9, 117.6, 63.9, 35.6; MS(ESI) for (M+H)+: 469.5.

Example 2

Preparation of Compound Hydroxytyrosol p-phenylenedicarboxylate (bis(3,4-dihydroxyphenethyl) 1,4-phenylenedicarbamate, Compound of Formula (I))

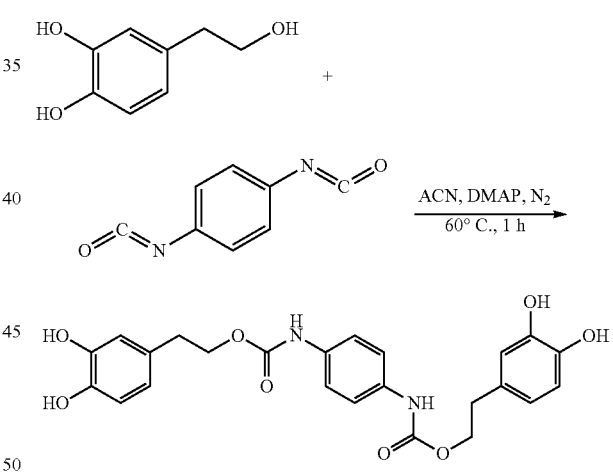

120.3 mg (0.78 mmol) hydroxytyrosol and 3.7 mg (0.03 mmol) DMAP (dimethylaminopyridine) were dissolved in 50 mL of acetonitrile in a 100 mL reactor to form a reaction mixture under nitrogen atmosphere. 50 mg (0.31 mmol) 1,4-phenylene diisocyanate in 5 mL acetonitrile was slowly added dropwise to the reaction liquid by a separatory funnel. The reaction mixture was then heated at 60° C. for 1 hour. Thin layer chromatography was used to track the reaction to completion. The reaction mixture was concentrated under reduced pressure to give a crude product. The crude product was purified by silica gel fresh chromatography, eluting with petroleum ether:ethyl acetate=6:1 as eluent, and the eluent was concentrated under reduced pressure and dried to obtain 82.5 mg hydroxytyrosol p-phenylenedicarboxylate, a yield of 56.84%.

Example 3

Preparation of Compound Hydroxytyrosol p-phenylenedicarboxylate (bis(3,4-dihydroxyphenethyl) 1,4-phenylenedicarbamate, Compound of Formula (I))

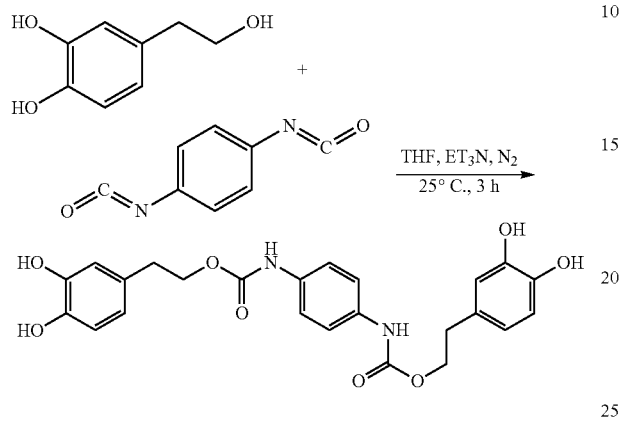

105.9 mg (0.68 mmol) hydroxytyrosol and 42 μL (0.30 mmol) triethylamine were dissolved in 50 mL of tetrahydrofuran in a 100 mL reactor to form a reaction mixture under nitrogen atmosphere. 50 mg (0.31 mmol) 1,4-phenylene diisocyanate in 5 mL tetrahydrofuran was slowly added dropwise to the reaction liquid by a separatory funnel. The reaction mixture was then heated at 25° C. for 3 hours. Thin layer chromatography was used to track the reaction to completion. The reaction mixture was concentrated under reduced pressure to give a crude product. The crude product was purified by silica gel fresh chromatography, eluting with petroleum ether:ethyl acetate=6:1 as eluent, and the eluent was concentrated under reduced pressure and dried to obtain 86.2 mg hydroxytyrosol p-phenylenedicarboxylate, a yield of 59.37%.

Example 4

Preparation of Compound Hydroxytyrosol p-phenylenedicarboxylate (bis(3,4-dihydroxyphenethyl) 1,4-phenylenedicarbamate, Compound of Formula (I))

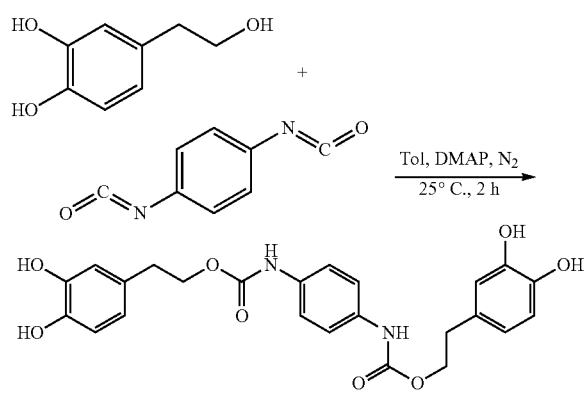

120.3 mg (0.78 mmol) hydroxytyrosol and 3.7 mg (0.03 mmol) DMAP were dissolved in 50 mL of toluene in a 100 mL reactor to form a reaction mixture under nitrogen atmosphere. 50 mg (0.31 mmol) 1,4-phenylene diisocyanate in 5 mL toluene was slowly added dropwise to the reaction liquid by a separatory funnel. The reaction mixture was then heated at 25° C. for 2 hours. Thin layer chromatography was used to track the reaction to completion. The reaction mixture was concentrated under reduced pressure to give a crude product. The crude product was purified by silica gel fresh chromatography, eluting with petroleum ether:ethyl acetate=6:1 as eluent, and the eluent was concentrated under reduced pressure and dried to obtain 90.2 mg hydroxytyrosol p-phenylenedicarboxylate, a yield of 62.10%.

Example 5

Preparation of Compound Hydroxytyrosol p-phenylenedicarboxylate (bis(3,4-dihydroxyphenethyl) 1,4-phenylenedicarbamate, Compound of Formula (I))

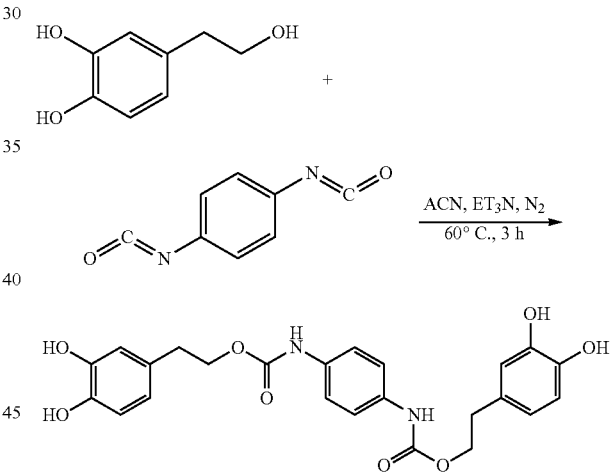

105.9 mg (0.68 mmol) hydroxytyrosol and 42 μL (0.30 mmol) triethylamine were dissolved in 50 mL of acetonitrile in a 100 mL reactor to form a reaction mixture under nitrogen atmosphere. 50 mg (0.31 mmol) 1,4-phenylene diisocyanate in 5 mL acetonitrile was slowly added dropwise to the reaction liquid by a separatory funnel. The reaction mixture was then heated at 60° C. for 3 hours. Thin layer chromatography was used to track the reaction to completion. The reaction mixture was concentrated under reduced pressure to give a crude product. The crude product was purified by silica gel fresh chromatography, eluting with petroleum ether:ethyl acetate=6:1 as eluent, and the eluent was concentrated under reduced pressure and dried to obtain 99.5 mg hydroxytyrosol p-phenylenedicarboxylate, a yield of 68.55%.

Example 6

Preparation of Compound Hydroxytyrosol p-phenylenedicarboxylate (bis(3,4-dihydroxyphenethyl) 1,4-phenylenedicarbamate, Compound of Formula (I))

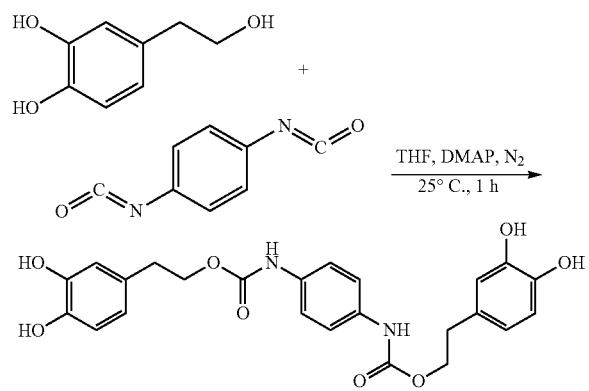

120.3 mg (0.78 mmol) hydroxytyrosol and 3.7 mg (0.03 mmol) DMAP were dissolved in 50 mL of tetrahydrofuran in a 100 mL reactor to form a reaction mixture under nitrogen atmosphere. 50 mg (0.31 mmol) 1,4-phenylene diisocyanate in 5 mL tetrahydrofuran was slowly added dropwise to the reaction liquid by a separatory funnel. The reaction mixture was then heated at 25° C. for 1 hour. Thin layer chromatography was used to track the reaction to completion. The reaction mixture was concentrated under reduced pressure to give a crude product. The crude product was purified by silica gel fresh chromatography, eluting with petroleum ether:ethyl acetate=6:1 as eluent, and the eluent was concentrated under reduced pressure and dried to obtain 67.1 mg hydroxytyrosol p-phenylenedicarboxylate, a yield of 46.19%.

Example 7

The Antioxidant Activity of the Hydroxytyrosol p-phenylenedicarboxylate Measured by a DPPH Radical Scavenging Activity Assay 2,2-Diphenyl-1-picryl hydrazyl (DPPH) is an organic compound composed of a stable organic radical. In the DPPH molecule, due to the presence of multiple electron-withdrawing —$NO_2$ and large $\pi$ bonds of the benzene ring, nitrogen free radical is stabilized. Its methanol solution is purple and has a maximum absorption peak at 517 nm. After the addition of an antioxidant, DPPH captures an electron to be paired with the free electron, and the purple fades and turns into a yellow substance. The absorption at 517 nm disappears, and the degree of fading is quantitatively related to the number of electrons it captures. Based on this principle, a spectrophotometer is used to detect the change of the absorbance of the DPPH radical and the sample solution, and the ability of the sample to provide hydrogen atoms and scavenge free radicals can be measured.

Preparation of DPPH solution: measuring exact amount of 2,2-diphenyl-1-picryl hydrazyl (DPPH) and dissolving in toluene to prepare a 0.2 mmolL/L DPPH solution, stored at 0° C. in dark.

Preparation of test solution: Vc (positive control), hydroxytyrosol p-phenylenedicarboxylate (sample) and hydroxytyrosol (control). The sample solution was subjected to gradient dilution with toluene, and two sets of controls were separately dissolved in a test tube with a certain amount of toluene to prepare the same concentration gradient as the sample. The corresponding two groups of control solutions were obtained (gradient settings are shown in Table 1).

TABLE 1

Dilution gradient of the test solution

| Number | Test solution | Concentration gradient/ppm |
|---|---|---|
| Vc | Vc | 1.76, 8.80, 21.12, 42.24, 79.20, 112.64, 281.60, 492.80, 792.00, 915.20 |
| A | Hydroxytyrosol p-phenylenedicarboxylate | 1.76, 8.80, 21.12, 42.24, 79.20, 112.64, 281.60, 492.80, 792.00, 915.20 |
| B | Hydroxytyrosol | 1.76, 8.80, 21.12, 42.24, 79.20, 112.64, 281.60, 492.80, 792.00, 915.20 |

Specific Steps:

Sample liquid absorbance measurement: Take 2 mL of sample solution (Table 1 Vc, B), add 2 mL of DPPH solution with concentration of $2*10^{-4}$ moL/L, mix and react in the dark at room temperature for 30 min, adjust to zero with toluene, and measure at 517 nm. The absorbance Ai was simultaneously measured for the absorbance Aj of 2 mL of toluene mixed with 2 mL of the sample solution and the absorbance Ao of 2 mL of DPPH solution mixed with 2 mL of toluene (The experimental results are shown in Table 2).

TABLE 2 absorbance test results of each test solution

| Sample | Absorbance | \multicolumn{10}{c}{Concentration/ppm} |
|---|---|---|---|---|---|---|---|---|---|---|---|
| | | 1.76 | 8.80 | 21.12 | 42.24 | 79.20 | 112.64 | 281.60 | 492.80 | 792.00 | 915.20 |
| Vc | Ai | 0.718 | 0.624 | 0.222 | 0.142 | 0.091 | 0.078 | 0.076 | 0.070 | 0.074 | 0.065 |
| | Aj | 0.068 | 0.061 | 0.050 | 0.054 | 0.069 | 0.057 | 0.062 | 0.062 | 0.066 | 0.059 |
| | Ao | | | | | | 0.846 | | | | |
| A | Ai | 0.775 | 0.741 | 0.620 | 0.548 | 0.321 | 0.226 | 0.203 | 0.167 | 0.139 | 0.119 |
| | Aj | 0.048 | 0.049 | 0.060 | 0.057 | 0.055 | 0.059 | 0.060 | 0.051 | 0.043 | 0.041 |
| | Ao | | | | | | 0.812 | | | | |
| B | Ai | 0.294 | 0.218 | 0.810 | 0.739 | 0.630 | 0.580 | 0.403 | 0.365 | 0.268 | 0.254 |
| | Aj | 0.053 | 0.046 | 0.047 | 0.039 | 0.060 | 0.055 | 0.041 | 0.046 | 0.035 | 0.037 |
| | Ao | | | | | | 0.935 | | | | |

Clearance calculation: clearance rate (%)=[1−(Ai−Aj)/Ao]*100%

TABLE 3

DPPH clearance rate experiment results

| Concentration/ppm | Clearance rate/% (n = 3) | | |
| --- | --- | --- | --- |
| | Vc | A | B |
| 1.76 | 23.16 | 10.45 | 7.42 |
| 8.80 | 33.47 | 14.80 | 8.16 |
| 21.12 | 79.63 | 31.06 | 18.43 |
| 42.24 | 89.55 | 39.54 | 25.10 |
| 79.20 | 97.42 | 67.22 | 38.99 |
| 112.64 | 97.53 | 79.43 | 43.87 |
| 281.60 | 98.29 | 82.35 | 61.25 |
| 492.80 | 99.06 | 85.67 | 65.88 |
| 792.00 | 99.10 | 88.12 | 75.03 |
| 915.20 | 99.28 | 90.37 | 76.76 |

According to the results of Tables 1 to 3 and FIG. 1, hydroxytyrosol p-phenylenedicarboxylate has a significant scavenging effect on DPPH in a concentration-dependent manner. Its DPPH clearance rate is from 10.45% (1.76 ppm) to 90.37% (915.20 ppm). Compared with hydroxytyrosol (B) alone, hydroxytyrosol p-phenylenedicarboxylate (A) has much better DPPH radical scavenging activity at same concentration. In addition, compared with the positive control Vc group, hydroxytyrosol p-phenylenedicarboxylate (A) has similar DPPH radical scavenging activity at same concentration. These experimental results show that hydroxytyrosol p-phenylenedicarboxylate has excellent antioxidant activity and a good application prospect.

What is claimed is:

1. A method of preparing a compound of the following formula (I), comprising:

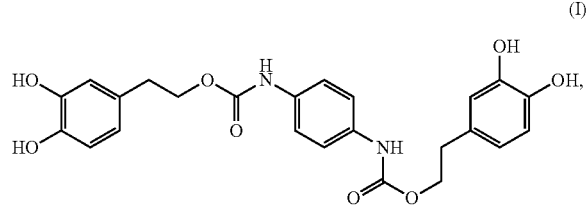 [SMILES: O=C(Nc1ccc(NC(=O)OCCc2ccc(O)c(O)c2)cc1)OCCc1ccc(O)c(O)c1]

(I)

reacting the compound of formula (II) with the compound of formula (III) to obtain the compound of formula (I):

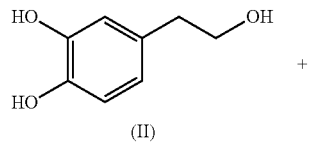

(II)

+

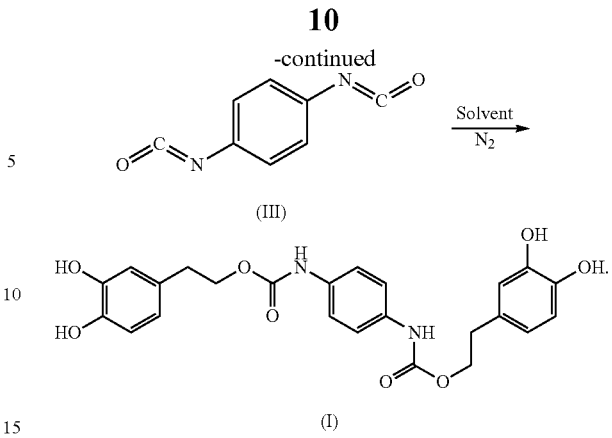

2. The method of claim 1, wherein the reaction of the compound of formula (II) with the compound of formula (III) comprises the following steps:

placing the compound of formula (II) and the compound of formula (III), in a molar ratio of 2.2:1 to 2.5:1, in a reactor to form a reaction mixture;

adding an organic solvent and a catalyst to the reaction mixture under nitrogen atmosphere;

heating the reaction mixture at 25-60° C. for 1-3 hours under sonication;

concentrating the reaction mixture under reduced pressure to give a crude product; and purifying the crude product using silica gel fresh chromatography, eluting with a mixture of ethyl acetate and petroleum ether solvent to obtain the compound formula (I).

3. The method of claim 2, wherein the organic solvent is toluene, acetonitrile or tetrahydrofuran.

4. The method of claim 3, wherein the organic solvent is toluene.

5. The method of claim 2, wherein the molar ratio of the compound of formula (II) and the compound of formula (III) is 2.2:1.

6. The method of claim 2, wherein the catalyst is triethylamine or 4-dimethylaminopyridine.

7. The method of claim 6, wherein the catalyst is triethylamine.

8. The method of claim 2, wherein the reaction mixture is heated at 60° C.

9. The method of claim 2, wherein the reaction mixture is heated for 2 hours.

10. The method of claim 2, wherein the mixture of petroleum ether and ethyl acetate has a volume ratio of 6:1.

* * * * *